US006107278A

United States Patent [19]
Schnepf et al.

[11] Patent Number: 6,107,278
[45] Date of Patent: Aug. 22, 2000

[54] **POLYNUCLEOTIDE ENCODING LEPIDOPTERAN ACTIVE TOXIN PS86I2 DERIVED FROM *BACILLUS THURINGIENSIS* AND METHODS OF USING PS86I2**

[75] Inventors: H. Ernest Schnepf; Kenneth E. Narva, both of San Diego; Judy Muller-Cohn, Del Mar, all of Calif.

[73] Assignee: Mycogen Corporation, San Diego, Calif.

[21] Appl. No.: 09/041,991

[22] Filed: Mar. 13, 1998

Related U.S. Application Data

[60] Provisional application No. 60/040,512, Mar. 13, 1997.

[51] Int. Cl.[7] .......................... C07K 14/00; C07H 17/00; C12P 21/06
[52] U.S. Cl. ...................... 514/12; 536/23.71; 435/69.1; 435/410; 435/320.1; 800/302
[58] Field of Search .............................. 536/23.1, 23.71; 514/12; 435/69.1, 320.1, 325, 253.2, 410; 800/302

[56] References Cited

U.S. PATENT DOCUMENTS

| | | |
|---|---|---|
| 4,448,885 | 5/1984 | Schnepf et al. . |
| 4,467,036 | 8/1984 | Schnepf et al. . |
| 4,797,276 | 1/1989 | Herrnstadt et al. . |
| 4,853,331 | 8/1989 | Herrnstadt et al. . |
| 4,918,006 | 4/1990 | Ellar et al. . |
| 4,948,734 | 8/1990 | Edwards et al. . |
| 4,990,332 | 2/1991 | Payne et al. . |
| 5,039,523 | 8/1991 | Payne et al. . |
| 5,073,632 | 12/1991 | Donovan ................................ 536/27 |
| 5,093,120 | 3/1992 | Edwards et al. . |
| 5,126,133 | 6/1992 | Payne et al. . |
| 5,151,363 | 9/1992 | Payne . |
| 5,164,180 | 11/1992 | Payne et al. . |
| 5,169,629 | 12/1992 | Payne et al. . |
| 5,204,237 | 4/1993 | Gaertner et al. . |
| 5,236,843 | 8/1993 | Narva et al. . |
| 5,262,399 | 11/1993 | Hickle et al. . |
| 5,270,448 | 12/1993 | Payne . |
| 5,273,746 | 12/1993 | Payne et al. . |
| 5,281,530 | 1/1994 | Sick et al. . |
| 5,322,932 | 6/1994 | Narva et al. . |
| 5,350,577 | 9/1994 | Payne . |
| 5,426,049 | 6/1995 | Sick et al. . |
| 5,439,881 | 8/1995 | Narva et al. . |
| 5,506,099 | 4/1996 | Carozzi et al. . |
| 5,686,069 | 11/1997 | Payne et al. . |

FOREIGN PATENT DOCUMENTS

| | | |
|---|---|---|
| 9314641 | 8/1993 | WIPO . |
| 9405771 | 3/1994 | WIPO . |
| 9424264 | 10/1994 | WIPO . |
| 9605314 | 2/1996 | WIPO . |
| 9800546 | 1/1998 | WIPO . |

OTHER PUBLICATIONS

Sasaki, J. (1996) "*Bacillus thuringiensis* DNA" Database/EMBL, abstract.

Beegle, C.C., T. Yamamoto (1992) "History of *Bacillus thuringiensis* Berliner Research and Development" Can. Entomologist. 124:587–616.

Dankocsik, C. et al. (1990) "Activation of a Cryptic Crystal Protein Gene of *Bacillus thuringiensis* Subspecies *kurstaki* by Gene Infusion and Determination of the Crystal Protein Insecticidal Specificty" Molecular Microbiology 4(12):2087–2094.

Wu, D. et al. (1991) "Sequence of an Operon Containing a Novel δ–Endotoxin Gene from *Bacillus thuringiensis*" FEMS Microbiology Letters 81:31–36.

Widner, William R. et al. (1989) "Two Highly Related Insecticidal Crystal Proteins of *Bacillus thuringiensis* Subsp. *kurstaki* Posses Different Host Range Specificites" Journal of Bacteriology 171(2):965–974.

Donovan, William P. et al. (1988) "Amino Acid Sequences and Entomocidal Activity of the P2 Crystal Protein: An Insect Toxin from *Bacillus thuringiensis* var. *kurstaki*" The Journal of Biological Chemistry 263(1):561–567.

Donovan, William P. et al. (1989) 264 Journal of Biological Chemistry 4740 (corrected p. 564, Fig. 4 of 263 JBC 561–567).

Gaertner, F. H. et al. (1988) "Current Applied Recombinant DNA Projects" TIBTECH 6:S4–S7.

Couch, T. L. (1980) "Mosquito Pathogenicity of *Bacilus thuringiensis* var. *israelenis*" Developments in Industrial Microbiology 22:61–76.

Beegle, C. C. (1978) "Use of Entomogenous Bacteria in Agroecosystems" Developments in Industrial Microbiology 20:97–104.

Krieg, A. et al. (1983) "*Bacillus thuringiensis* var. *tenebrionis*, a new pathotype effective against the larvae of Coleoptera" Z. ang. Ent. 96:500–508.

Höfte, H. et al. (1989) "Insecticidal Crystal Proteins of *Bacillus thuringiensis*" Microbiological Reivew 52(2):242–245.

Feitelson, J. S. et al. (1992) "*Bacillus thuringiensis*: Insects and Beyond" Bio/Technology 10:271–275.

Lambert, B. et al. (1996) "A *Bacillus thuringiensis* Insecticidal Crystal Protein with a High Activity against Members of the Family Noctuidae" Appl. Environ. Microbiol. 62(1):80–86.

(List continued on next page.)

*Primary Examiner*—Karen Cochrane Carlson
*Attorney, Agent, or Firm*—Saliwanchik, Lloyd & Saliwanchik

[57] ABSTRACT

The subject invention pertains to novel insecticidal toxins and genes which encode these toxins. Also disclosed are novel nucleotide primers for the identification of genes encoding toxins active against pests. The primers are usefull in PCR techniques to produce gene fragments which are characteristic of genes encoding these toxins.

12 Claims, No Drawings

OTHER PUBLICATIONS

Gaertner, F. H. (1989) "Cellular Delivery Systems for Insecticidal Proteins: Living and Non–Living Microorganisms" Controlled Delivery of Crop Protection Agents, R. M. Wilkins (ed.), Taylor and Francis (pub.), New York and London, 1990, pp. 245–255.

Schnepf, H. E. et al. (1981) "Cloning and expression of the *Bacillus thuringiensis* crystal protein gene in *Escherichia coli*" Proc. Natl. Acad. Sci. USA 78:2893–2897.

Gleave et al. (1991) "Identification of an insecticidal crystal protein from *Bacillus thuringiensis* DSIR517 with significant sequence differences from previously described toxins" JGM 138:55–62.

Smulevitch et al. (1991) "Nucleotide sequence of a novel δ–endotoxin gene cryIg of *Bacillus thuringiensis* ssp. *galleriae*" FEBS Lett. 336:79–82.

Shevelev et al. (1993) "Primary structure of cryX, the novel δ–endotoxin–related gene from *Bacillus thuringiensis* ssp. *galleriae*" FEBS Lett. 293:25–26.

POLYNUCLEOTIDE ENCODING LEPIDOPTERAN ACTIVE TOXIN PS86I2 DERIVED FROM *BACILLUS THURINGIENSIS* AND METHODS OF USING PS86I2

CROSS-REFERENCE TO A RELATED APPLICATION

This application claims priority from U.S. provisional application Ser. No. 60/040,512 filed Mar. 13, 1997.

BACKGROUND OF THE INVENTION

The soil microbe *Bacillus thuringiensis* (B.t.) is a Gram-positive, spore-forming bacterium traditionally characterized by parasporal crystalline protein inclusions. These inclusions often appear microscopically as distinctively shaped crystals. The proteins can be highly toxic to pests and specific in their toxic activity. Certain B.t. toxin genes have been isolated and sequenced, and recombinant DNA-based B.t. products have been produced and approved for use. In addition, with the use of genetic engineering techniques, new approaches for delivering B.t. toxins to agricultural environments are under development, including the use of plants genetically engineered with endotoxin genes for insect resistance and the use of stabilized intact microbial cells as B. t. toxin delivery vehicles (Gaertner, F. H., L. Kim [1988] *TIBTECH* 6:S4–S7; Beegle, C. C., T. Yamamoto, "History of *Bacillus thuringiensis* Berliner research and development," *Can. Ent.* 124:587–616). Thus, isolated B.t. toxin genes are becoming commercially valuable.

Until the last fifteen years, commercial use of B.t. pesticides has been largely restricted to a narroa range of lepidopteran (caterpillar) pests. Preparations of the spores and crystals of *B. thuringiensis subsp. kurstaki* have been used for many years as commercial insecticides for lepidopteran pests. For example, *B. thuringiensis var. kurstaki* HD-1 produces a crystalline δ-endotoxin which is toxic to the larvae of a number of lepidopteran insects.

Investigators, have now discovered B.t. pesticides with specificities for a much broader range of pests. For example, other species of B.t., namely *israelensis* and *morrisoni* (a.k.a. *tenebrionis*, a.k.a. B.t. M-7, a.k.a. B.t. san diego), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255.). See also Couch, T. L. (1980) "Mosquito Pathogenicity of *Bacillus thuringiensis var. israelensis*," *Developments in Industrial Microbiology* 22:61–76; and Beegle, C. C. (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508 describe *Bacillus thuringiensis var. tenebrionis*, which is reportedly active against two beetles in the order Coleoptera. These art the Colorado potato beetle, *Leptinotarsa decemlineata*, and *Agelastica alni*.

More recently, new subspecies of B.t. have been identified, and genes responsible for active δ-endotoxin proteins have been isolated (Höfte, H., H. R. Whiteley [1989] *Microbiological Reviews* 52(2):242–255). Höfte and Whiteley classified B. t. crystal protein genes into four major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported (Feitelson, J. S., J. Payne, L. Kim [1992] *Bio/Technology* 10:271–275). CryV has been proposed to designate a class of toxin genes that are nematode-specific. Lambert et al. (Lambert, B., L. Buysse, C. Decock, S. Jansens, C. Piens, B. Saey, J. Seurinck, K. van Audenhove, J. Van Rie, A. Van Vliet, M. Peferoen [1996] *Appl. Environ. Microbiol* 62(1):80–86) describe the characterization of a Cry9 toxin active against lepidopterans. Published PCT applications WO 94/05771 and WO 94/24264 also describe B.t. isolates active against lepidcpteran pests. Gleave et al. ([1991] *JGM* 138:55–62), Shevelev et al. ([1993] *FEBS Lett.* 336:79–82; and Smulevitch et al. ([1991] *FEBS Lett.* 293:25–26) also describe B.t. toxins. Many other classes of B.t. genes have now been identified.

The cloning and expression of a B.t. crystal protein gene in *Escherichia coli* has been described in the published literature (Schnepf, H. E., H. R. Whiteley [1981] *Proc. Natl. Acad. Sci. USA* 78:2893–2897.). U.S. Pat. No. 4,448,885 and U.S. Pat. No. 4,467,036 both disclose the expression of B.t. crystal protein in *E. coli*. U.S. Pat. Nos. 4,990,332; 5,039,523; 5,126,133; 5,164,180; and 5,169,629 are among those which disclose B.t. toxins having activity against lepidopterans. PCT application WO96/05314 discloses PS86W1, PS86V1, and other B.t. isolates active against lepidopteran pests. The PCT patent applications published as WO94/24264 and WO94/05771 describe B.t. isolates and toxins active against lepidopteran pests. B.t. proteins with activity against members of the family Noctuidae are described by Lambert et al., supr2. U.S. Pat. Nos. 4,797,276 and 4,853,331 disclose *B. thuringiensis* strain *tenebrionis* which can be used to control coleopteran pests in various environments. U.S. Pat. No. 4,918,006 discloses B.t. toxins having activity against dipterans. U.S. Pat. No. 5,151,363 and U.S. Pat. No. 4,948,734 disclose certain isolates of B.t. which have activity against nematodes. Other U.S. Pat. Nos. which disclose activity against nematodes include 5,093,120; 5,236,843; 5,262,399; 5,270,448; 5,281,530; 5,322,932; 5,350,577; 5,426,049; and 5,439,881.

A cry2Aa gene from HD263 kurstaki is disclosed by Donovan et al. in 264 *JBC* 4740 (1989). Another cry2Aa gene and a cry2Ab gene, from HD1 kurstaki, are disclosed by Widner & Whiteley, 171 *J Bac.* 965–974 (1989). Another cry2Ab gene from HD1 kurstaki is disclosed by Dankocsik et al. in 4 *Mol. Micro* 2087–2094 (1990). A cry2Ac gene from B. t. S-1 (shanghai) is disclosed by Wu et al. in 81 FEMS 31–36 (1991).

An isolate known as PS192M4 is disclosed in U.S. Pat. No. 5,273,746 as having activity against lice.

The PS86I2 isolate is disclosed in U.S. Pat. No. 5,686,069 as having activity against lepidopterans. PS91C2 is exemplified therein as producing a CryIF(b)-type of lepidopteran-active toxin, the sequence of which is disclosed therein.

Sequence in formation for a lepidopteran-active toxin from HD525 and the sequence of a lepidopteran-active toxin from HD573 are disclosed in WO 98/00546. Those toxins are not Cry2-type toxins.

As a result of extensive research and investment of resources, other patents have issued for new B.t. isolates and new uses of B.t. isolates. See Feitelson et al., supra, for a review. However, the discovery of new B.t. isolates and new uses of known B.t. isolates remains an empirical, unpredictable art. U.S. Pat. No. 5,506,099 describes methods for identifying unknown B.t. isolates. U.S. Pat. No. 5,204,237 describes specific and universal probes for the isolation of B.t. toxin genes. These patents, however, do not describe the probes and primers of the subject invention.

BRIEF SUMMARY OF THE INVENTION

The subject invention concerns materials and methods useful in the control of non-mammalian pests and, particularly, plant pests. In a specific embodiment, the subject invention provides new toxins useful for the control of lepidopterans. A preferred embodiment of the subject invention further provides nucleotide sequences which encode the novel lepidopteran-active toxins of the subject invention.

The subject invention further provides nucleotide sequences and methods useful in the identification and characterization of novel genes which encode pesticidal toxins. In one embodiment, the subject invention concerns unique nucleotide sequences which are useful as primers in PCR techniques. The primers produce characteristic gene fragments which can be used in the identification and isolation of novel toxin genes. A further aspect of the subject invention is the use of the disclosed nucleotide sequences as probes to detect genes encoding B.t. toxins which are active against lepidopterans.

Further aspects of the subject invention include other novel genes and toxins identified using the methods and nucleotide sequences disclosed herein, in addition to the novel genes and toxins specifically disclosed herein. The genes thus identified encode toxins active against lepidopterans. Similarly, the isolates capable of producing these toxins have activity against these pests. Thus, the subject invention further provides new *Bacillus thuringiensis* isolates having pesticidal activities which are found with the primers and probes according to, the subject invention.

In one embodiment of the subject invention, B.t. isolates can be cultivated under conditions resulting; in high multiplication of the microbe. After treating the microbe to provide single-stranded genomic nucleic acid, the DNA can be contacted with the primers of the invention and subjected to PCR amplification. Characteristic fragments of toxin-encoding genes are amplified by the procedure, thus identifying the presence of the toxin-encoding gene(s).

In a preferred embodiment, the subject invention concerns plants cells transferred with at least one polynucleotide sequence of the subject invention such that the transformed plant cells express, pesticidal toxins in tissues consumed by the target pests. Such transformation of plants can be accomplished using techniques well known to those skilled in the art and would typically involve modification of the gene to optimize expression of the toxin in plants. In addition, the toxins of the subject invention may be chimeric toxins produced by combining portions of multiple toxins.

As an alternative to the transformation of plants, the B. t. isolates and toxins of the subject invention, or recombinant microbes expressing the toxins described herein, can be used to control pests. In this regard, the invention includes the treatment of substantially intact B. t. cells, and/or recombinant cells containing the expressed toxins of the invention, treated to prolong the pesticidal activity when the substantially intact cells are applied to the environment of a target pest. The treated cell acts as a protective coating for the pesticidal toxin. The toxin becomes active upon ingestion by a target insect.

BRIEF DESCRIPTION OF THE SEQUENCES

SEQ ID NO. 1 is a forward primer useful according to the subject invention.

SEQ ID NO. 2 is a reverse primer useful according to the subject invention.

SEQ ID NO. 3 is a nucleotide sequence which encodes the 192M4 toxin.

SEQ ID NO. 4 is the predicted amino acid sequence of the 192M4 toxin.

SEQ ID NO. 5 is a nucleotide sequence which encodes the HD573 toxin.

SEQ ID NO. 6 is the predicted amino acid sequence of the HD573 toxin.

SEQ ID NO. 7 is a nucleotide sequence which encodes the HD525 toxin.

SEQ ID NO. 8 is the predicted amino acid sequence of the HD525 toxin.

SEQ ID NO. 9 is a nucleotide sequence which encodes the 86I2 toxin.

SEQ ID NO. 10 is the predicted amino acid sequence of the 86I2 toxin.

DETAILED DISCLOSURE OF THE INVENTION

The subject invention concerns materials and methods for the control of non-mammalian pests. In specific embodiments, the subject invention pertains to new *Bacillus thuringiensis* toxins, and genes encoding toxins, which have activity against lepidopterans. The subject invention concerns not only the polynucleotide sequences which encode these toxins, but also the use of these polynucleotide sequences to produce recombinant hosts which express the toxins. The subject invention further concerns novel nucleotide sequences that are useful as primers and probes for *Bacillus thuringiensis* (B.t.) genes that encode pesticidal toxins, especially lepidopteran-active toxins. The subject invention still further concerns novel methods for identifying and characterizing B.t. isolates, toxins, and genes with useful properties.

The new toxins and polynucleotide sequences provided here are defined according to several parameters. One critical characteristic of the toxins described herein is pesticidal activity. In a specific embodiment, these toxins have activity against lepidopteranpests. The toxins and genes of the subject invention can be further defined by their amino acid and nucleotide sequences. The sequences of the molecules can be defined in terms of homology or identity to certain exemplified sequences as well as in terms of the ability to hybridize with, or be amplified by, certain exemplified probes and primers. The toxins provided herein can also be identified based on their immunoreactivity with certain antibodies.

Methods have been developed for making useful chimeric toxins by combining portions of B.t. crystal proteins. The portions which are combined need not, themselves, be pesticidal so long as the combination of portions creates a chimeric protein which is pesticidal. This can be done using restriction enzymes, as described in, for example, European Patent 0 228 838; Ge, A. Z., N. L. Shivarova, D. H. Dean (1989) *Proc. Natl. Acad. Sci. USA* 86:4037–4041; Ge, A. Z., D. Rivers, R. Milne, D. H. Dean (1991) *J Biol. Chem.* 266:17954–17958; .Schnepf, H. E., K. Tomczak, J. P. Ortega, H. R. Whiteley (1990) *J Biol. Chem.* 265:20923–23930; Honee, G., D. Convents, J. Van Rie, S. Jansens, M. Peferoen, B. Visser (1991) *Mol. Microbiol.* 5:2799–2806. Alternatively, recombination using cellular recombination mechanisms can be used to achieve similar results. See, for example, Caramori, T., A. M. Albertini, A. Galizzi (1991) *Gene* 98:37–44; Widner, W. R., H. R. Whiteley (1990) *J. Bacteriol.* 172:2826–2832; Bosch, D., B. Schipper, H. van der Kliej, R. A. de Maagd, W. J. Slickema (1994) *Biotechnology* 12:915–918. A number of other methods are known in the art by which such chimeric DNAs can be made. The subject invention is meant to include clijieric proteins that utilize the novel sequences identified in the subject application.

With the teachings provided herein, one skilled in the art could readily produce and use the various toxins and polynucleotide sequences described herein.

B.t. isolates useful according to the subject invention have been deposited in the permanent collection of the Agricultural Research Service Patent Culture Collection (NRRL), Northern Regional Research Center, 1815 North University Street, Peoria, Ill. 61604, USA. The culture repository numbers of the B. t. strains are as follows:

TABLE 1

| B.t. Isolate | Repository No. | Deposit Date |
| --- | --- | --- |
| PS86I2 | NRRL B-21957 | March 12, 1998 |
| PS192M4 | NRRL B-18932 | December 27, 1991 |

TABLE 2

| Source Isolate | E. Coli Strain | Plasmid | Repository No. | Deposit Date |
| --- | --- | --- | --- | --- |
| PS192M4 | MR908 | pMYC2586 | NRRL B-21631 | October 17, 1996 |
| HD573 | MR909 | pMYC2587 | NRRL B-21632 | October 17, 1996 |
| HD525 | MR910 | pMYC2588 | NRRL B-21633 | October 17, 1996 |

Cultures have been deposited under conditions that assure that access to the cultures is available during; the pendency of this patent application to one determined by the Commissioner of Patents and Trademarks to be entitled thereto under 37 CFR 1.14 and 35 U.S.C. 122. The deposits will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the culture(s). The depositor acknowledges the duty to replace the deposit(s) should the depository be unable to finish a sample when requested, due to the condition of a deposit. All restrictions on the availability to the public of the subject culture deposits will be irrevocably removed upon the granting of a patent disclosing them.

The isolates, HD525 and HD573 are available from the USDA-ARS NRRL Culture Collection, Peoria, Ill.

Following is a table which provides characteristics of certain isolates useful according to the subject invention.

TABLE 3

| Description of native B.t. strains | | | |
| --- | --- | --- | --- |
| Strain | Inclusion Type | H-Serotype | SDS-PAGE protein profile |
| 192M4 | Amorphic | 4a4b, sotto | 130, 68 |
| 86I2 | Bipyramidal | 8 | 130, 30, 15 |
| HD525 | Bipyramidal with ORT | not motile | 130 |
| HD573 | Bipyramidal | not motile | 140, 130, 70 |

Genes and toxins.

The genes and toxins usefull according to the subject invention include not only the full length sequences but also fragments of these sequences, variants, mutants, and fusion proteins which retain the characteristic pesticidal activity of the novel toxins specifically exemplified herein. Chimeric genes and toxins, produced by combining portions from more than one B.t. toxin or gene, may also be utilized according to the teachings of the subject invention. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the exemplified toxins.

It should be apparent to a person skilled in this art that genes encoding active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal3 1 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from B.t. isolates and/or DIA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other B. t. toxins.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA. sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

Certain toxins of the subject invention have been specifically exemplified herein. Since these toxins are merely exemplary of the toxins of the subject invention, it should be readily apparent that the subject invention also relates to variants or equivalents of novel genes and toxins having the same or similar pesticidal activity of the exemplified novel toxins. Equivalent toxins will have amino acid homology with a novel exemplified toxin. These equivalent genes and toxins will typically have greater than 60% identity with the sequences specifically exemplified herein; preferably, there will be more than 75% identity, more preferably greater than 80%, most preferably greater than 90%, and the identity can be greater than 95%. The amino acid homology will be highest in critical regions of the toxin which account for biological activity or are involved in the determination of three-dimensional configuration which ultimately is responsible for the biological activity. In this regard, conservative substitutions whereby an amino acid of one class is replaced with another amino acid of the same type fall within the scope of the subject invention so long as the substitution does not materially alter the biological activity. of the compound. Table 4 provides a listing of examples of amino acids belonging to each class.

TABLE 4

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The toxins of the subject invention can also be characterized in terms of the shape and location of toxin inclusions, which are described above. Although novel crystal proteins are specifically exemplified herein, isolates for use according to the subject invention can be grown under conditions that facilitate the secretion of toxins. Thus, the supernatant from these cultures can be used to obtain toxins according to the subject invention. Thus, the subject invention is not limited to crystal proteins; useful soluble proteins are also contemplated.

As used herein, reference to "isolated" polynucleotide and/or "purified" toxins refers to these molecules when they are not associated with the other molecules with which they would be found in nature. Thus, reference to "isolated and purified" signifies the involvement of the "hand of man" as described herein. Chimeric toxins and genes also involve the "hand of man."

The use of oligonucleotide probes provides a method for identifying the toxins and genes of the subject invention, and additional novel genes and toxins. Probes provide a rapid method for identifying toxin-encoding genes. The nucleotide segments which are used as probes according to the invention can be synthesized using a DNA synthesizer and standard procedures, for example.

Recombinmnt hosts.

The toxin-encoding genes of the subject invention can be introduced into a wide variety of microbial or plant hosts. Expression of the toxin gene results, directly or indirectly, in the production and maintenance of the pesticide. With suitable microbial hosts, e.g., Pseudomonas, the microbes can be applied to the situs of the pest, where they will proliferate and be ingested. The result is a control of the pest. Alternatively, the microbe hosting the toxin gene can be killed and treated under conditions that prolong the activity of the toxin and stabilize the cell. The treated cell, which retains the toxic activity, then can be applied to the environment of the target pest.

A wide variety of methods are available for introducing a B.t. gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Alteratively,, a plant transformed to express a toxin of the subject invention can be used to contact the: target pest with the toxin. Synthetic genes which are functionally equivalent to the novel toxins of the subject invention can also be used to transform hosts. Methods for the production of synthetic genes can be found in, for example, U.S. Pat. No. 5,380,831.

Treatment of cells.

As mentioned above, B.t. or recombinant cells expressing a B.t. toxin can be treated to prolong the toxin activity and stabilize the cell. The pesticide microcapsule that is formed comprises the B.t. toxin within a cellular structure that has been stabilized and will protect the toxin when the microcapsule is applied to the environment of the target pest. Methods for treatment of microbial cells are disclosed in U.S. Pat. Nos. 4,695,455 and 4,695,462, which are incorporated herein by reference.

Growth of cells.

The cellular host containing the B.t. insecticidal gene may be grown in any convenient nutrient medium, where the DNA construct provides a selective advantage, providing for a selective medium so that substantially all or all of the cells retain the B.t. gene. These cell, may then be harvested in accordance with conventional ways. Alternatively, the cells can be treated prior to harvesting.

The B.t. cells of the invention can be cultured using standard art media and fermentation techniques. Upon completion of the fermentation cycle the bacteria can be harvested by first separating the B.t. spores and crystals from the fermentation broth by means well known in the art. Any B.t. spores and crystals can be recovered employing well-known techniques and used as a conventional δ-endotoxin B.t. preparation. For example, the spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art. Alternately, the supernatant from the fermentation process can be used to obtain toxins according to the present invention. Soluble, secreted toxins are then isolated and purified employing well-known techniques.

Methods and formulations for control of pests.

Control of lepidopterans using the isolates, toxins, and genes of the subject invention can be accomplished by a variety of methods known to those skilled in the art. These methods include, for example, the application of B.t. isolates to the pests (or their location), the application of recombinant microbes to the pests (or their locations), and the transformation of plants with genes which encode the pesticidal toxins of the subject invention. Recombinant microbes may be, for example, a B.t., *E coli,* or Pseudomonas. Transformations can be made by those skilled in the art using standard techniques. Materials necessary for these transformations are disclosed herein or are otherwise readily available to the skilled artisan.

Formulated bait granules containing an attractant and toxins of the B.t. isolates, or recombinant microbes comprising the genes obtainable from the B.t. isolates disclosed herein, can be applied to the soil. Formulated product can also be applied as a seed-coating or root treatment or total plant treatment at later stages of the crop cycle. Plant and soil treatments of B.t. cells may be employed as liquids, wettable powders, granules, or dusts, by mixing with various inert materials, such as inorganic minerals (phyllosilicates, carbonates, sulfates, phosphates, and the like) or botanical materials (powdered corncobs, rice hulls, walnut shells, and the like).

As would be appreciated by a person skilled in the art, the pesticidal concentration will vary widely depending upon the nature of the particular formulation, particularly whether it is a concentrate or to be used directly. The pesticide will be present in at least about 1% by weight and may be 100% by weight. The dry formulations will have from about 1–95% by height of the pesticide while the liquid formulations will generally be from about 1–60% by weight of the solids in the liquid phase. The formulations will generally have from about $10^2$ to about $10^4$ cells/mg. These formulations that contain cells will be administered at about 50 mg (liquid or dry) to 1 kg or more per hectare.

The formulations can be applied to the environment of the pest, e.g., soil and foliage, by spraying, dusting, sprinkling, or the like.

Mutants.

Mutants of novel isolates obtainable according to the invention can be made by procedures well known in the art. For example, an asporogenous mutant can be obtained through emthylmethane sulfonate (EMS) mutagenesis of an isolate. The mutants can be made using ultraviolet light and nitrosoguanidine by procedures well known in the art.

Polynucleotide probes.

Hybridization may be used to test whether two pieces of DNA are complementary in their base sequences. It is this hybridization mechanism which facilitates the use of probes of the subject invention to readily detect and characterize DNA sequences of interest. The probes may be RNA or DNA. The probe will normally have at least about 10 bases, more usually at least about 18 bases, and may have up to about 50 bases or more, usually not having more than about 200 bases if the probe is made synthetically. However, longer Frobes can readily be utilized, and such probes can be, for example, several kilobases in length. The probes may be labeled utilizing techniques which are well known to those skilled in this art.

One approach for the use of the subject invention as probes entails first identifying by Southern blot analysis of a gene bank of the B.t. isolate all DNA segments homologous with the disclosed nucleotide sequences. Thus, it is possible, without the aid of biological analysis, to know in advance the probable activity of many new B.t. isolates, and of the individual endotoxin gene products expressed by a given B.t. isolate. Such a probe analysis provides a rapid method for identifying potentially commercially valuable insecticidal endotoxin genes within the multifarious subspecies of B.t.

The particular hybridization technique is not essential to the subject invention. As improvements are made in hybridization techniques, they can be readily applied.

The nucleotide segments of the subject invention which are used as probes can be synthesized by use of DNA synthesizers using standard procedures. In the use of the nucleotide segments as probes, the particular probe is labeled with any suitable label known to those skilled in the art, including radioactive and non-radioactive labels.

Various degrees of stringency of hybridization can be employed. The more severe the conditions, the greater the complementary that is required for duplex formation. Severity can be controlled by temperature, probe concentration, probe length, ionic strength, time, and the like. Preferably, hybridization is conducted under stringent conditions by techniques well known in the art, as described, for example, in Keller, G. H., M. M. Manak (1987) *DNA Probes,* Stockton Press, New York, N.Y., pp. 169–170. As used herein "stringent" conditions for hybridization refers to conditions which achieve the same, or about the same, degree of specificity of hybridization as the conditions employed by the current applicants. Specifically, hybridization of immobilized DNA on Southern blots with 32P-labeled gene-specific probes was performed by standard methods (Maniatis et al.). In general, hybridization and subsequent washes were carried out under stringent conditions that allowed for detection of target sequences with homology to the exemplified toxin genes. For double-stranded. DNA gene probes, hybridization was carried out overnight at 20–25° C. below the melting temperature (Tm) of the DNA hybrid in 6× SSPE, 5× Denhardt's solution, 0.1% SDS. 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology,* R. Wu, L. Grossman and K. Moldave [eds.] Academic Press, New York 100:266–285).

Tm=8 1.5° C.+16.6Log[Na+]+0.41 (% G+C)–0.6 1 (% formamide)-600/length of duplex in base pairs.

Washes are typically carried out as follows:

(1) Twice at room temperature for 15 minutes in 1× SSPE, 0.1% SDS (low stringency wash).

(2) Once at Tm-20° C. for 15 minutes in 0.2× SSPE, 0.1% SDS (moderate stringency wash).

For oligonucleotide probes, hybridization was carried out overnight at 10–20° C. below the melting temperature (Tm) of the hybrid in 6× SSPE, 5× Denhardt's solution, 0.1% SDS, 0.1 mg/ml denatured DNA. Tm for oligonucleotide probes was determined by the following formula:

Tm (° C.)=2(number T/A base pairs)+4(number G/C base pairs) (Suggs, S. V., T. Miyake, E. H. Kawashime, M. J. Johnson, K. Itakura, and R. B. Wallace [1981] *ICN-UCLA Symp. Dev. Biol. Using Purified Genes,* D. D. Brown [ed.], Academic Press, New York, 23:683–693).

Washes were typically carried out as follows:

(1) Twice at room temperature for 15 minutes 1× SSPE, 0.1% SDS (low stringency wash).

(2) Once at the hybridization temperature for 15 minutes in 1× SSPE, 0.1% SDS (moderate stringency wash).

PCR technology.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions and deletions can be produced in a given primer by methods known to an ordinarily skilled artisan.

Following are examples which illustrate procedures for practicing the invention. These examples should not be construed as limiting. All percentages are by weight and all solvent mixture proportions are by volume unless otherwise noted.

EXAMPLE 1

General Culturing Methods for B.t. Isolates Referred to Herein

A subculture of B.t. isolates, or mutants thereof, can be used to inoculate the following peptone, glucose, salts medium:

Bacto Perftone 7.5 g/l
Glucose 1.0 g/l
$KH_2PO_4$ 3.4 g/l
$K_2HPO_4$ 4.35 g/l
Salt Solulion 5.0 ml/l
$CaCl_2$ Solution 5.0 ml/l
pH7.2
Salts Solution (100 ml)
$MgSO_4 \cdot 7H_2O$ 2.46 g
$MnSO_4 \cdot H_2O$ 0.04 g
$ZnSO_4 \cdot 7H_2O$ 0.28 g
$FeSO_4 \cdot 7H_2O$ 0.40g
$CaCl_2$ Solution (100 ml)
$CaCl_2 \cdot 2H_2O$ 3.66 g The salts solution and $CaCl_2$ solution are filter-sterilized and added to the autoclaved and cooked broth at, the time of inoculation. Flasks are incubated at 30° C. on a rotary shaker at 200 rpm for 64 hx.

The above Procedure can be readily scaled up to large fermentors by procedures well known in the art.

The B.t. toxins obtainable with the above fermentation, can be isolated by procedures well known in the art. A frequently-used procedure is to subject the harvested fermentation broth to separation techniques, e.g., centrifugation.

EXAMPLE 2

Identification of Genes Encoding Novel Lepidopteran-Active Bacillus thuringiensis Toxin A DNA-based polymerase chain reaction (PCR) technique was used for the identification and classification of novel toxin genes in B.t. strains. Two PCR primers useful for the identification of toxin genes (Forward 1 and Reverse 1) were designed. These primers contain degenerate codons in the nucleotide positions designated by ambiguity codes, and have restriction sites incorporated into the 5' ends to enable molecular cloning of novel, amplified DNA fragments. The sequences of these oligonucleotides are:

Forward 1

5'-GGCCACTAGT AAAAAGGAGA TAACCATGAA TAATGTATTG AATARYGGAA T-3' (SEQ ID NO. 1)

Reverse 1

5'-GGCCCTCGAG GGTACCCAAA CCTTAATAAA GTGGTGRAAK ATTAGTTGG-3' (SEQ ID NO. 2)

Primers were synthesized using an Applied Biosystems model 381A DNA synthesizer. Toxin genes were then amplified from genomic B.t. DNA templates with these primers by standard PCR protocols (Perkin-Elmer) as follows: DNA templates for PCR were prepared from B.t. cells grown for 18 hours on agar plates. A loopful of cells were resuspended in TE buffer containing 50 µg/ml proteinase K and incubated at 55° C. for 15 minutes. The cell suspensions were then boiled for 15 minutes. Cellular debris was pelleted in a microfuge, and the supernatant containing the DNA was transferred to a clean tube. Ten µl of this crude genomic DNA template was then used in a 100 µl PCR reaction mixture comprised of 50 mM KCl, 10 mM Tris-Cl (pH 8.3), 1.5 mM $MgCl_2$, 200 µM each dNTP, 0.1–1 µM each primer, and 2.5 units of Taq DNA polymerase.

EXAMPLE 3

Restriction Fragment Length Polymorphism (RFLP) Analysis of Bacillus thuringiensis Toxin Genes PCR amplification using primer pair 1 (Forward 1 and Reverse 1) is expected to yield DNA fragments approximately 1900 base pairs in length from B.t. toxin genes related to the cry2 subfamily. Simplified gene sequences were discriminated from one another, and from known genes, by comparing the sizes of DNA restriction fragments generated by digestion of the PCR products with, for example, BglII, HincIII, ScaI, or HinFI (Table 5). Briefly, approximately 0.25–1 µg DNA from a PCR reaction was digested with a given restriction enzyme and elect ophoresed on an agarose or polyacrylamide gel. The gel was then stained with ethidiun bromide and DNA restriction fragments were visualized by illumination with UV light at 260–280 nm. The sizes of the restriction fragments were determined by their electrophoretic mobility relative to standard DNA fragments of known sizes. In some strains the number of fragments suggested the presence of more than one amplified toxin gene.

TABLE 5

Sizes of restriction fragments obtained by digestion of PCR-amplified DNA

| B.t. toxin gene (GenBank Accession Number) or source strain | Restriction enzyme | Approximate DNA fragment size (base pairs) |
| --- | --- | --- |
| cry2Aa1 (M31738) | BglII | 616, 1333 |
| cry2Aa1 (M31738) | ScaI | 937, 1012 |
| cry2aA1 (M31738) | HinFI | 51, 223, 340, 363, 375, 597 |
| cry2Ab1 (M23724) | HincII | 815, 1134 |
| cry2Ab1 (M23724) | HinFI | 51, 105, 112, 223, 263, 363, 832 |
| cry2Ac (X57252) | ScaI | 185, 1731 |
| cry2Ac (X57252) | HinFI | 112, 223, 244, 293, 360, 684 |
| PS192M4 | BglII | 616, 1339 |
| PS192M4 | HincII | 813, 1135 |
| PS192M4 | ScaI | 943, 1012 |
| PS192M4 | HinFI | 51, 112, 175, 188, 223, 261, 269, 340, 363, 597, 1161 |
| HD573 | HincII | 813, 1135 |
| HD573 | ScaI | 185, 1734 |
| HD573 | HinFI | 112, 223, 244, 261, 293, 360, 363, 687, 1161 |
| HD525 | HincII | 813, 1135 |
| HD525 | ScaI | 185, 1734 |
| HD525 | HinFI | 51, 112, 223, 244, 261, 293, 360, 363, 687, 1161 |
| PS86I2 | HincII | 793, 1109 |
| PS86I2 | HinFI | 51, 112, 263, 341, 1135 |

Genes from strains with unique restriction fragment polymorphisms were cloned into pBluescript SK (Stratagene, San Diego, Calif.) and transformed into E. coli NM522 for further study. Subcultures of recombinant E. coli strains harboring these plasmids encoding these new toxins were deposited in the permanent collection of the Patent Culture Collection (NRRL), Regional research Center, 1815 North University Street, Peoria, Ill. 61604 on Oct. 17, 1996.

EXAMPLE 4

DNA Sequence Analysis of Novel Toxin Genes

DNA templates for automated sequencing were amplified by PCR using vector primers. These DNA templates were sequenced using Applied Biosystems (Foster City, Calif.) automated sequencing methodologies. Novel toxin gene sequences (SEQ ID NOs. 3, 5, 7, and 9) and their respective predicted polypeptide sequences (SEQ ID NOs. 4, 6, 8, and 10) are listed in Table (5, below.

TABLE 6

| Source Strain | Nucleotide SEQ ID NO. | Peptide SEQ ID NO. |
|---|---|---|
| 192M4 | 3 | 4 |
| HD573 | 5 | 6 |
| HD525 | 7 | 8 |
| 86I2 | 9 | 10 |

EXAMPLE 5

Heterologous Expression of Novel B.t. Toxins in *Pseudomonas fluorescens*

The toxin genes listed above were engineered into plasmid vectors by standard DNA cloning methods, and transformed into *Pseudomonas fluorescens*. Recombinant bacterial strains were grown in shake flasks for production of toxin for expression and quantitative bioassay against a variety of lepidopteran insect pests.

EXAMPLE 6

Activity of Novel B.t. Toxins Against *Heliothis virescens* (Fabricius) and *Helicoverpa zea* (Boddie)

Suspensions of powders containing recombinant clones according to the subject invention were prepared by individually mixing powder samples with distilled water and agitating vigorously. Suspensions were mixed with toasted soy flour artificial diet at a rate of 6 mL suspension plus 54 mL diet, yielding a concentration of 100 μg toxin/mL finished diet. After vortexing, this mixture was poured into plastic trays with compartmentalized 3 ml wells (Nutrend Container Corporation, Jacksonville, Fla.). A water blank containing no recombinant toxin served as the control. First instar larvae (USDA-ARS, Stoneville, Miss.) were placed singly into the diet mixture. Wells were then sealed with "MYLAR" sheeting (ClearLam Packaging, Ill.) using a tacking iron, and several pinholes were made in each well to provide gas exchange. Larvae were held at 25° C. in a 14:10 (light:dark) holding room. Mortality was recorded after six days.

TABLE 7

*H. virescens* larval mortality with toxins in diet incorporation bioassays

| Source Strain | Percent Mortality |
|---|---|
| 192M4 | 87 |
| HD573 | 80 |
| HD525 | 17 |
| water control | 8 |

TABLE 8

*H. zea* larval mortality with toxins in diet incorporation bioassays

| Source Strain | Percent Mortality |
|---|---|
| 192M4 | 19 |
| HD525 | 21 |
| water control | 8 |

EXAMPLE 7

Activity of Novel B.t. Toxins Against *Ostrinia nubilalis* (Huebner)

Test suspensions were prepared in 0.5 ml or 1 ml volumes by mixing powder samples with distilled water. Test suspensions were held in sterile-packaged 12×75 mm polypropylene tubes with snap cap (e.g., Elkay Laboratory Products). Tubes were placed in hot block (e.g., Fisher Scientific Hot Block) prewarmed to 34–35° C. approximately 15 minutes (or less) prior to dispensation of the diet. The test suspensions were vortexed for a few seconds just prior to the addition of the diet to the 12×75 mm tube. To the 0.5 ml or 1 ml volumes was added 1 or 2 ml diet, respectively. The diet was measured and squirted into the tube by means of a 3 ml or 5 ml syringe with rubber tip plunger. The tube with the test suspension and diet was vortexed for 5–10 seconds or until visibly mixed. The toxin/diet suspension was then dispensed into a pre-labeled 96-well assay tray.

Diet was dispensed into the 96-well assay tray by means of a repeater pipettor with a 1.25 ml capacity pipet tip at a 4 setting for approximately 100 μl per well.

Larvae were infested one per well and sealed with waxy adhesive covering by heat treatment with iron (Oliver Products, Mich.). Bioassays were held at 26–28° C., and data were collected in 7 days.

TABLE 9

*O. nubilalis* larval mortality with toxins in diet incorporation bioassays

| Source Strain | Percent Mortality |
|---|---|
| 192M4 | 50 |
| HD573 | 90 |
| water control | 8 |

EXAMPLE 8

Insertion of Toxin Genes Into Plants

One aspect of the subject invention is the transformation of plants with genes encoding the insecticidal toxin of the subject invention. The transformed plants are resistant to attack by the target pest.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higherplants. The vectors comprise, for example, pBR322, pUC series, M13mp series, pACYC184, (to. Accordingly, the sequence encoding the B. t. toxin can be inserted into the vector at a statable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of IDNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al, *Crit. Rev. Plant Sci.* 4:1–46);; and An et al. (1985) *EMBO J* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques inch Lde transformation with T-DNA using *Agrobacterium tumefaciens* or *Agrobacterium rhizogenes* as transformation agent, fusion, injection, biolistics (microparticle bombardment), or electroporation as well as other possible methods. If Agrobacteria are used for the transformation, the DNA to be inserted has to be cloned into special plasmids, namely either into art intermediate vector or into a binary vector. The intermediate vectors can be integrated into the Ti or Ri plasmid by homologous recombination owing to sequences that are ILomologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the right and left T-DNA border regions. They can be transformed directly into Agrobacteria (Holsters et al. [1978] *Mol. Gen. Genet.* 163:181–187). The Agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, meristematic tissue, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives. In biolistics transformation, plasmid DNA or linear DNA can be employed.

The transformed cells are regenerated into morphologically normal plants in the usual manner. If a transformation event involves a germ line cell, the inserted DNA and corresponding phenotypic trait(s) will be transmitted to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831. Also, advantageously, plants encoding a truncated toxin will be used. The truncated toxin typically will encode about 55% to about 80% of the full length toxin. Methods for creating synthetic B.t. genes for use in plants are known in the art.

All of the U.S. patents cited herein are hereby incorporated by reference.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. An isolate polynucleotide which encodes a lepidopteran-active toxin wherein said toxin comprises the amino acid sequence of SEQ ID NO. 10 or a lepidopteran-toxic fragment thereof.

2. The polynucleotide, according to claim 1, wherein said toxin comprises the amino acid sequence of SEQ ID NO. 10.

3. The polynucleotide, according to claim 1, wherein said polynucleotide comprises the nucleotide sequence of SEQ ID NO. 9 or a fragment thereof that is sufficient to encode a lepidopteran-toxic protein.

4. The polynucleotide, according to claim 1, wherein said polynucleotide comprises he nucleotide sequence of SEQ ID NO. 9.

5. A transformed host which expresses a polynucleotide encoding a lepidopteran-active toxin wherein said toxin comprises the amino acid sequence of SEQ ID NO. 10 or a lepidopteran-toxic fragment thereof.

6. The host, according to claim 5, wherein said host is a plant or a plant cell.

7. The host according to claim 5 wherein said toxin comprises the amino acid sequence of SEQ ID NO. 10.

8. A method for controlling a lepidopteran pest wherein said method comprises contacting said pest with a toxin comprising the amino acid sequence SEQ ID NO. 10 or a lepidopteran-toxic fragment thereof.

9. The method according to claim 8, wherein said lepidopteran pest is an *Ostrinia nubilalis*.

10. The method according to claim 8, wherein said lepidopteran pest is a *Heliothis virescens*.

11. The method according to claim 8, wherein said lepidopteran pest is a *Helicoverpa zea*.

12. The method according to claim 8 wherein said toxin comprises the amino acid sequence of SEQ ID NO. 10.

* * * * *

UNITED STATES PATENT AND TRADEMARK OFFICE
CERTIFICATE OF CORRECTION

PATENT NO.   : 6,107,278
DATED        : August 22, 2000
INVENTOR(S)  : H. Ernest Schnepf, Kenneth E. Narva, Judy Muller-Cohn It is certified that error appears in the above-identified patent and that said Letters Patent is hereby corrected as shown below:

Column 1,
Line 31, "narroa range" should read -- narrow range --.
Line 56, "art" should read -- are --.

Column 2,
Line 29, "supr2." should read -- supra. --.
Line 42, "J" should read -- J. --.

Column 3,
Line 41, "transferred" should read -- transformed --.

Column 4,
Line 40, "lepidopteranpests" should read -- lepidopteran pests --.
Line 58, "-17958; .Schnepf," should read -- -17958; Schnepf, --.
Line 59, "J" should read -- J. --.
Line 67, "Slickema" should read -- Stickema --.

Column 5,
Line 3, "clijieric" should read -- chimeric --.
Line 35, "during; the" should read -- during the --.

Column 6,
Line 39, "Bal3 1" should read -- *Bal*31 --.
Line 53, "B. t." should read -- B.t. --.
Line 60, "DNA. sequences" should read -- DNA sequences --.

Column 7,
Line 21, "activity. of" should read -- activity of --.

Column 8,
Line 14, "Alternatively,, a" should read -- Alternatively, a --.
Line 15, "the: target" should read -- the target --.

Column 9,
Line 21, "height" should read -- weight --.
Line 34, "emthylmethane" should read -- ethylmethane --.
Line 47, "Frobes" should read -- probes --.

UNITED STATES PATENT AND TRADEMARK OFFICE
CERTIFICATE OF CORRECTION

PATENT NO. : 6,107,278
DATED : August 22, 2000
INVENTOR(S) : H. Ernest Schnepf, Kenneth E. Narva, Judy Muller-Cohn It is certified that error appears in the above-identified patent and that said Letters Patent is hereby corrected as shown below:

Column 10,
Line 7, "complementary" should read -- complementarity --.
Line 30, "Tm = 8 1.5°" should read -- Tm = 81.5° --.

Column 11,
Line 28, "64 hx." should read -- 64 hr. --.
Line 29, "Procedure" should read -- procedure --.
Line 40, "Toxin" should read -- Toxins --.

Column 12,
Line 13, "Simplified" should read -- Amplified --.
Line 18, "elect ophoresed" should read -- electrophoresed --.

Column 13,
Line 5, "Table 15, below" should read -- Table 6, below --.

Column 14,
Line 64, "higherplants" should read -- higher plants --.
Line 66, "(to." should read -- etc. --.
Line 67, "statable" should read -- suitable --.

Column 15,
Line 16, "IDNA" should read -- T-DNA --.
Line 20, "-46);;" should read -- -46; --.
Line 21, "J" should read -- J. --.
Line 32, "inch Lde" should read -- include --.
Line 39, "artintermediate" should read -- an intermediate --.
Line 42, "ILomologous" should read -- homologous --.

Column 16,
Line 13, "leef" should read -- leaf --.

Column 37,
Line 60, "isolate" should read -- isolated --.

UNITED STATES PATENT AND TRADEMARK OFFICE
CERTIFICATE OF CORRECTION

PATENT NO. : 6,107,278
DATED : August 22, 2000
INVENTOR(S) : H. Ernest Schnepf, Kenneth E. Narva, Judy Muller-Cohn It is certified that error appears in the above-identified patent and that said Letters Patent is hereby corrected as shown below:

Column 38,
Line 62: "he" should read -- the --.

Signed and Sealed this

Thirteenth Day of November, 2001

Attest:

NICHOLAS P. GODICI
Attesting Officer   Acting Director of the United States Patent and Trademark Office

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 51 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

GGCCACTAGT AAAAAGGAGA TAACCATGAA TAATGTATTG AATARYGGAA T            51

(2) INFORMATION FOR SEQ ID NO:2:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GGCCCTCGAG GGTACCCAAA CCTTAATAAA GTGGTGRAAK ATTAGTTGG               49

(2) INFORMATION FOR SEQ ID NO:3:

(i) SEQUENCE CHARACTERISTICS:
        (A) LENGTH: 1908 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

ATGAATAATG TATTGAATAG TGGAAGAACA ACTATTTGTA ATGCGTATAA TGTAGTGGCT     60

CACGATCCAT TTAGTTTTGA ACATAAATCA TTAGATACCA TCCAAGAAGA ATGGATGGAG    120

TGGAAAAGAA CAGATCATAG TTTATATGTA GCTCCTGTAG TCGGAACTGT GTCTAGTTTT    180

CTGCTAAAGA AAGTGGGGAG TCTAATTGGA AAAAGGATAT TGAGTGAATT ATGGGGGTTA    240

ATATTTCCTA GTGGTAGTAC AAATCTAATG CAAGATATTT AAGAGAGAC AGAACAATTC     300

CTAAATCAAA GACTTAATAC AGACACCCTT GATCGTGTAA ATGCAGAATT GGAAGGGCTC    360

CAAGCGAATA TAAGGGAGTT TAATCAACAA GTAGATAATT TTTTAAACCC TACTCAAAAC    420

CCTGTTCCTT TATCAATAAC TTCTTCAGTT AATACAATGC AGCAATTATT TCTAAATAGA    480

TTACCCCAGT TCCAGATACA AGGATACCAG TTGTTATTAT TACCTTTATT TGCACAGGCA    540

GCCAATATGC ATCTTTCTTT TATTAGAGAT GTTATTCTTA ATGCAGATGA ATGGGCATT     600

TCAGCAGCAA CACTACGTAC GTATCGAGAC TACCTGAGAA ATTATACAAG AGATTATTCT    660

AATTATTGTA TAAATACGTA TCAAACTGCG TTTAGAGGGT TAAACACCCG TTTACACGAT    720

ATGTTAGAAT TTAGAACATA TATGTTTTTA AATGTATTTG AATATGTATC CATTTGGTCA    780

TTGTTTAAAT ATCAGAGTCT TATGGTATCT TCTGGCGCTA ATTTATATGC TAGTGGTAGT    840

GGACCACAGC AGACACAATC ATTTACTGCA CAAAACTGGC CATTTTTATA TTCTCTTTTC    900

CAAGTTAATT CGAATTATAT ATTATCTGGT ATTAGTGGTA ATAGGCTTTC TACTACCTTC    960

CCTAATATTG GTGGTTTACC GGGTAGTACT ACAATTCATT CATTGAACAG TGCCAGGGTT   1020

AATTATAGCG GAGGAGTTTC ATCTGGTCTC ATAGGGGCGA CTAATCTCAA TCACAACTTT   1080

AATTGCAGCA CGGTCCTCCC TCCTTTATCA ACACCATTTG TTAGAAGTTG GCTGGATTCA   1140

GGTACAGATC GAGAGGGCGT TGCTACCTCT ACGACTTGGC AGACAGAATC CTTCCAAATA   1200

ACTTCAGGTT TAAGGTGTGG TGCTTTTCCT TTTTCAGCTC GTGGAAATTC AAACTATTTC   1260

CCAGATTATT TTATCCGTAA TATTTCTGGG GTTCCTTTAG TTATTAGAAA CGAAGATCTA   1320

ACAAGACCGT TACACTATAA CCAAATAAGA AATATAGAAA GTCCTTCGGG AACACCTGGT   1380

```
GGATTACGAG CTTATATGGT ATCTGTGCAT AACAGAAAAA ATAATATCTA TGCCGCTCAT      1440

GAAAATGGTA CTATGATTCA TTTGGCACCG GAAGATTATA CAGGATTTAC TATATCACCA      1500

ATACATGCCA CTCAAGTGAA TAATCAAACT CGAACATTTA TTTCTGAAAA ATTTGGAAAT      1560

CAAGGTGATT CCTTAAGATT TGAACAAAGT AACACGACAG CTCGTTATAC GCTTAGAGGG      1620

AATGGAAATA GTTACAATCT TTATTTAAGG GTATCTTCTC TAGGAAATTC CACTATTCGA      1680

GTTACTATAA ACGGAAGAGT TTATACTGTT CCAAATGTTA ATACAAATAT AAATAACGAT      1740

GGAGTCATTG ATAATGGAGC TCGTTTTTCA GATATTAATA TCGGTAATGT AGTAGCAAGT      1800

GATAATACTA ATGTACCGTT AGATATAAAC GGGACATTAA GTTCTGGAAC TCAATTTGAG      1860

CTTATGAATA TTATGTTTGT TCCAACTAAT CTTCCACCAC TTTATTAA                   1908
```

(2) INFORMATION FOR SEQ ID NO:4:

(i) SEQUENCE CHARACTERISTICS:
        (A) LENGTH: 635 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met Asn Asn Val Leu Asn Ser Gly Arg Thr Thr Ile Cys Asn Ala Tyr
 1               5                  10                  15

Asn Val Val Ala His Asp Pro Phe Ser Phe Glu His Lys Ser Leu Asp
            20                  25                  30

Thr Ile Gln Glu Glu Trp Met Glu Trp Lys Arg Thr Asp His Ser Leu
        35                  40                  45

Tyr Val Ala Pro Val Val Gly Thr Val Ser Ser Phe Leu Leu Lys Lys
    50                  55                  60

Val Gly Ser Leu Ile Gly Lys Arg Ile Leu Ser Glu Leu Trp Gly Leu
65                  70                  75                  80

Ile Phe Pro Ser Gly Ser Thr Asn Leu Met Gln Asp Ile Leu Arg Glu
                85                  90                  95

Thr Glu Gln Phe Leu Asn Gln Arg Leu Asn Thr Asp Thr Leu Asp Arg
            100                 105                 110

Val Asn Ala Glu Leu Glu Gly Leu Gln Ala Asn Ile Arg Glu Phe Asn
        115                 120                 125

Gln Gln Val Asp Asn Phe Leu Asn Pro Thr Gln Asn Pro Val Pro Leu
    130                 135                 140

Ser Ile Thr Ser Ser Val Asn Thr Met Gln Gln Leu Phe Leu Asn Arg
145                 150                 155                 160

Leu Pro Gln Phe Gln Ile Gln Gly Tyr Gln Leu Leu Leu Pro Leu
                165                 170                 175

Phe Ala Gln Ala Ala Asn Met His Leu Ser Phe Ile Arg Asp Val Ile
                180                 185                 190

Leu Asn Ala Asp Glu Trp Gly Ile Ser Ala Ala Thr Leu Arg Thr Tyr
            195                 200                 205

Arg Asp Tyr Leu Arg Asn Tyr Thr Arg Asp Tyr Ser Asn Tyr Cys Ile
        210                 215                 220

Asn Thr Tyr Gln Thr Ala Phe Arg Gly Leu Asn Thr Arg Leu His Asp
225                 230                 235                 240

Met Leu Glu Phe Arg Thr Tyr Met Phe Leu Asn Val Phe Glu Tyr Val
                245                 250                 255
```

```
Ser Ile Trp Ser Leu Phe Lys Tyr Gln Ser Leu Met Val Ser Ser Gly
            260                 265                 270

Ala Asn Leu Tyr Ala Ser Gly Ser Gly Pro Gln Gln Thr Gln Ser Phe
            275                 280                 285

Thr Ala Gln Asn Trp Pro Phe Leu Tyr Ser Leu Phe Gln Val Asn Ser
            290                 295                 300

Asn Tyr Ile Leu Ser Gly Ile Ser Gly Asn Arg Leu Ser Thr Thr Phe
305                 310                 315                 320

Pro Asn Ile Gly Gly Leu Pro Gly Ser Thr Thr Ile His Ser Leu Asn
                325                 330                 335

Ser Ala Arg Val Asn Tyr Ser Gly Gly Val Ser Ser Gly Leu Ile Gly
                340                 345                 350

Ala Thr Asn Leu Asn His Asn Phe Asn Cys Ser Thr Val Leu Pro Pro
                355                 360                 365

Leu Ser Thr Pro Phe Val Arg Ser Trp Leu Asp Ser Gly Thr Asp Arg
                370                 375                 380

Glu Gly Val Ala Thr Ser Thr Thr Trp Gln Thr Glu Ser Phe Gln Ile
385                 390                 395                 400

Thr Ser Gly Leu Arg Cys Gly Ala Phe Pro Phe Ser Ala Arg Gly Asn
                405                 410                 415

Ser Asn Tyr Phe Pro Asp Tyr Phe Ile Arg Asn Ile Ser Gly Val Pro
                420                 425                 430

Leu Val Ile Arg Asn Glu Asp Leu Thr Arg Pro Leu His Tyr Asn Gln
                435                 440                 445

Ile Arg Asn Ile Glu Ser Pro Ser Gly Thr Pro Gly Gly Leu Arg Ala
                450                 455                 460

Tyr Met Val Ser Val His Asn Arg Lys Asn Asn Ile Tyr Ala Ala His
465                 470                 475                 480

Glu Asn Gly Thr Met Ile His Leu Ala Pro Glu Asp Tyr Thr Gly Phe
                485                 490                 495

Thr Ile Ser Pro Ile His Ala Thr Gln Val Asn Asn Gln Thr Arg Thr
                500                 505                 510

Phe Ile Ser Glu Lys Phe Gly Asn Gln Gly Asp Ser Leu Arg Phe Glu
                515                 520                 525

Gln Ser Asn Thr Thr Ala Arg Tyr Thr Leu Arg Gly Asn Gly Asn Ser
                530                 535                 540

Tyr Asn Leu Tyr Leu Arg Val Ser Ser Leu Gly Asn Ser Thr Ile Arg
545                 550                 555                 560

Val Thr Ile Asn Gly Arg Val Tyr Thr Val Pro Asn Val Asn Thr Asn
                565                 570                 575

Ile Asn Asn Asp Gly Val Ile Asp Asn Gly Ala Arg Phe Ser Asp Ile
                580                 585                 590

Asn Ile Gly Asn Val Val Ala Ser Asp Asn Thr Asn Val Pro Leu Asp
                595                 600                 605

Ile Asn Gly Thr Leu Ser Ser Gly Thr Gln Phe Glu Leu Met Asn Ile
                610                 615                 620

Met Phe Val Pro Thr Asn Leu Pro Pro Leu Tyr
625                 630                 635
```

(2) INFORMATION FOR SEQ ID NO:5:

(i) SEQUENCE CHARACTERISTICS:
        (A) LENGTH: 1872 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:5:

```
ATGAATAATG TATTGAATAG CGGAAGAAAT ACTACTTGTC ATGCACATAA TGTAGTTGCT      60

CATGATCCAT TTAGTTTTGA ACATAAATCA TTAAATACCA TAGAAAAAGA ATGGAAAGAA     120

TGGAAAAGAA CTGATCATAG TTTATATGTA GCCCCTATTG TGGGAACTGT GGGTAGTTTT     180

CTATTAAAGA AAGTAGGGAG TCTTGTTGGA AAAAGGATAC TGAGTGAGTT ACAGAATTTA     240

ATTTTTCCTA GTGGTAGTAT AGATTTAATG CAAGAGATTT AAGAGCGAC AGAACAATTC      300

ATAAATCAAA GGCTTAATGC AGACACCCTT GGTCGTGTAA ATGCAGAATT GGCAGGTCTT     360

CAAGCGAATG TGGCAGAGTT TAATCGACAA GTAGATAATT TTTTAAACCC TAATCAAAAC     420

CCTGTTCCTT TAGCAATAAT TGATTCAGTT AATACATTGC AGCAATTATT TCTAAGTAGA     480

TTACCACAGT TCCAGATACA AGGCTATCAA CTGTTATTAT TACCTTTATT TGCACAGGCA     540

GCCAATTTAC ATCTTTCTTT TATTAGAGAT GTCATCCTTA ATGCAGATGA ATGGGGCATT     600

TCAGCAGCAA CAGTACGCAC ATATAGAGAT CACCTGAGAA ATTTCACAAG AGATTACTCT     660

AATTATTGTA TAAATACGTA TCAAACTGCA TTTAGAGGTT TAAACACTCG TTTACACGAT     720

ATGTTAGAAT TTAGAACATA TATGTTTTTA AATGTATTTG AATATGTCTC TATCTGGTCG     780

TTATTTAAAT ATCAAAGCCT TCTAGTATCT TCCGGCGCTA ATTTATATGC GAGTGGTAGT     840

GGTCCAACAC AATCATTTAC AGCACATAAC TGGCCATTTT TATATTCTCT TTTCCAAGTT     900

AATTCTAATT ATGTATTAAA TGGTTTGAGT GGTGCTAGGA CCACCATTAC TTTCTCTAAT     960

ATTGGTGGTC TTCCCGGTTC TACCACAACT CAAACATTGC ATTTTGCGAG GATTAATTAT    1020

AGAGGTGGAG TGTCATCTAG CCGCATAGGT CAAGCTAATC TTAATCAAAA CTTTAACATT    1080

TCCACACTTT TCAATCCTTT ACAAACACCG TTTATTAGAA GTTGGCTAGA TTCTGGTACA    1140

GATCGGGAGG GCGTTGCCAC CTCTACAAAC TGGCAATCAG GAGCCTTTGA GACAACTTTA    1200

TTACGATTTA GCATTTTTTC AGCTCGTGGT AATTCGAACT TTTTCCCAGA TTATTTTATC    1260

CGTAATATTT CTGGTGTTGT TGGGACTATT AGCAACGCAG ATTTAGCAAG ACCTCTACAC    1320

TTTAATGAAA TAAGAGATAT AGGAACGACA GCAGTCGCTA GCCTTGTAAC AGTGCATAAC    1380

AGAAAAAATA ATATCTATGA CACTCATGAA AATGGTACTA TGATTCATTT AGCGCCAAAT    1440

GACTATACAG GATTTACCGT ATCTCCAATA CATGCCACTC AAGTAAATAA TCAAATTCGA    1500

ACGTTTATTT CCGAAAAATA TGGTAATCAG GGTGATTCCT TGAGATTTGA GCTAAGCAAC    1560

ACAACGGCTC GATACACACT TAGAGGGAAT GGAAATAGTT ACAATCTTTA TTAAGAGTA     1620

TCTTCAATAG GAAGTTCCAC AATTCGAGTT ACTATAAACG GTAGAGTTTA TACTGCAAAT    1680

GTTAATACTA CCACAAATAA TGATGGAGTA CTTGATAATG GAGCTCGTTT TTCAGATATT    1740

AATATCGGTA ATGTAGTGGC AAGTGCTAAT ACTAATGTAC CATTAGATAT ACAAGTGACA    1800

TTTAACGGCA ATCCACAATT TGAGCTTATG AATATTATGT TTGTTCCAAC TAATCCTTCA    1860

CCACTTTATT AA                                                        1872
```

(2) INFORMATION FOR SEQ ID NO:6:

(i) SEQUENCE CHARACTERISTICS:
            (A) LENGTH: 623 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

```
Met Asn Asn Val Leu Asn Ser Gly Arg Asn Thr Thr Cys His Ala His
1               5                   10                  15

Asn Val Val Ala His Asp Pro Phe Ser Phe Glu His Lys Ser Leu Asn
            20                  25                  30

Thr Ile Glu Lys Glu Trp Lys Glu Trp Lys Arg Thr Asp His Ser Leu
        35                  40                  45

Tyr Val Ala Pro Ile Val Gly Thr Val Gly Ser Phe Leu Leu Lys Lys
    50                  55                  60

Val Gly Ser Leu Val Gly Lys Arg Ile Leu Ser Glu Leu Gln Asn Leu
65                  70                  75                  80

Ile Phe Pro Ser Gly Ser Ile Asp Leu Met Gln Glu Ile Leu Arg Ala
                85                  90                  95

Thr Glu Gln Phe Ile Asn Gln Arg Leu Asn Ala Asp Thr Leu Gly Arg
                100                 105                 110

Val Asn Ala Glu Leu Ala Gly Leu Gln Ala Asn Val Ala Glu Phe Asn
            115                 120                 125

Arg Gln Val Asp Asn Phe Leu Asn Pro Asn Gln Asn Pro Val Pro Leu
    130                 135                 140

Ala Ile Ile Asp Ser Val Asn Thr Leu Gln Gln Leu Phe Leu Ser Arg
145                 150                 155                 160

Leu Pro Gln Phe Gln Ile Gln Gly Tyr Gln Leu Leu Leu Leu Pro Leu
                165                 170                 175

Phe Ala Gln Ala Ala Asn Leu His Leu Ser Phe Ile Arg Asp Val Ile
            180                 185                 190

Leu Asn Ala Asp Glu Trp Gly Ile Ser Ala Ala Thr Val Arg Thr Tyr
        195                 200                 205

Arg Asp His Leu Arg Asn Phe Thr Arg Asp Tyr Ser Asn Tyr Cys Ile
        210                 215                 220

Asn Thr Tyr Gln Thr Ala Phe Arg Gly Leu Asn Thr Arg Leu His Asp
225                 230                 235                 240

Met Leu Glu Phe Arg Thr Tyr Met Phe Leu Asn Val Phe Glu Tyr Val
                245                 250                 255

Ser Ile Trp Ser Leu Phe Lys Tyr Gln Ser Leu Leu Val Ser Ser Gly
                260                 265                 270

Ala Asn Leu Tyr Ala Ser Gly Ser Gly Pro Thr Gln Ser Phe Thr Ala
            275                 280                 285

His Asn Trp Pro Phe Leu Tyr Ser Leu Phe Gln Val Asn Ser Asn Tyr
        290                 295                 300

Val Leu Asn Gly Leu Ser Gly Ala Arg Thr Thr Ile Thr Phe Ser Asn
305                 310                 315                 320

Ile Gly Gly Leu Pro Gly Ser Thr Thr Gln Thr Leu His Phe Ala
                325                 330                 335

Arg Ile Asn Tyr Arg Gly Gly Val Ser Ser Ser Arg Ile Gly Gln Ala
            340                 345                 350

Asn Leu Asn Gln Asn Phe Asn Ile Ser Thr Leu Phe Asn Pro Leu Gln
        355                 360                 365

Thr Pro Phe Ile Arg Ser Trp Leu Asp Ser Gly Thr Asp Arg Glu Gly
    370                 375                 380

Val Ala Thr Ser Thr Asn Trp Gln Ser Gly Ala Phe Glu Thr Thr Leu
385                 390                 395                 400
```

```
        Leu Arg Phe Ser Ile Phe Ser Ala Arg Gly Asn Ser Asn Phe Phe Pro
                        405                 410                 415

Asp Tyr Phe Ile Arg Asn Ile Ser Gly Val Val Gly Thr Ile Ser Asn
                        420                 425                 430

Ala Asp Leu Ala Arg Pro Leu His Phe Asn Glu Ile Arg Asp Ile Gly
                        435                 440                 445

Thr Thr Ala Val Ala Ser Leu Val Thr Val His Asn Arg Lys Asn Asn
                        450                 455                 460

Ile Tyr Asp Thr His Glu Asn Gly Thr Met Ile His Leu Ala Pro Asn
        465                 470                 475                 480

Asp Tyr Thr Gly Phe Thr Val Ser Pro Ile His Ala Thr Gln Val Asn
                        485                 490                 495

Asn Gln Ile Arg Thr Phe Ile Ser Glu Lys Tyr Gly Asn Gln Gly Asp
                        500                 505                 510

Ser Leu Arg Phe Glu Leu Ser Asn Thr Thr Ala Arg Tyr Thr Leu Arg
                        515                 520                 525

Gly Asn Gly Asn Ser Tyr Asn Leu Tyr Leu Arg Val Ser Ser Ile Gly
                        530                 535                 540

Ser Ser Thr Ile Arg Val Thr Ile Asn Gly Arg Val Tyr Thr Ala Asn
        545                 550                 555                 560

Val Asn Thr Thr Thr Asn Asn Asp Gly Val Leu Asp Asn Gly Ala Arg
                        565                 570                 575

Phe Ser Asp Ile Asn Ile Gly Asn Val Val Ala Ser Ala Asn Thr Asn
                        580                 585                 590

Val Pro Leu Asp Ile Gln Val Thr Phe Asn Gly Asn Pro Gln Phe Glu
                        595                 600                 605

Leu Met Asn Ile Met Phe Val Pro Thr Asn Pro Ser Pro Leu Tyr
                        610                 615                 620

(2) INFORMATION FOR SEQ ID NO:7:

(i) SEQUENCE CHARACTERISTICS:
        (A) LENGTH: 1902 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

ATGAATAATG TATTGAATAG TGGAAGAAAT ACTATTTGTG ATGCGTATAA TGTAGTGGTT      60

CATGATCCAT TTAGTTTTCA ACATAAATCA TTAGATACCA TACAAAAAGA ATGGATGGAG     120

TGGAAAAAAG ATAATCATAG TTTATATGTA GATCCTATTG TTGGAACTGT GGCTAGTTTT     180

CTGTTAAAGA AATTGGGGAG CCTTATTGGA AAACGGATAC TGAGTGAATT ACGGAATTTA     240

ATATTTCCTA GTGGCAGTAC AAATCTAATG AAGATATTT TAAGAGAGAC AGAAAAATTC      300

CTAAATCAAA AACTTAATAC AGACACTCTT TCCCGTGTAA ATGCGGAATT GACAGGGCTG     360

CAAGCAAATG TAGAAGAGTT TAATCGACAA GTAGATAATT TTTGAACCC TAACCGAAAC      420

GCTGTTCCTT TATCAATAAC TTCTTCAGTT AATACAATGC AGCAATTATT TCTAAATAGA     480

TTATCCCAGT TCCAGATGCA AGGATACCAA CTGTTATTAT TACCTTTATT TGCACAGGCA     540

GCCAATTTAC ATCTTTCTTT TATTAGAGAT GTTATTCTTA ATGCAGAAGA ATGGGGCATT     600

TCAGCAGCAA CATTACGTAC GTATCAAAAT CACCTGAGAA ATTATACAAG AGATTACTCT     660

AATTATTGTA TAGATACGTA TCAAACTGCG TTTAGAGGTT TAAACACCCG TTTACACGAT     720
```

-continued

```
ATGTTAGAAT TTAGAACATA TATGTTTTTA AATGTATTTG AATATGTATC TATCTGGTCG        780

TTGTTTAAAT ATCAAAGTCT TCTAGTATCT TCTGGCGCTA ATTTATATGC AAGTGGTAGT        840

GGACCACAGC AGACCCAATT ATTTACTTCA CAAGACTGGC CATTTTTATA TTCTCTTTTC        900

CAAGTTAATT CGAATTATGT ATTATCCGGC TTTAGTGGGG CTAGTCTTTT TACTACCTTT        960

CCTAATATTG GTGGCTTACC TGGTTCTACT ACAACTCAAG CATTACTTGC TGCAAGGGTT       1020

AATTATAGTG GAGGAATTAC ATCTGGTAGT ATAGGGGGTT CTAATTTTAA TCAAAATTTT       1080

AATTGCAACA CGATATCGCC ACCTTTGTCA ACGTCATTTG TTAGAATTTG GCTAGATTCG       1140

GGTTCAGATC GACAGGGCGT TACTACCGTT ACAAATTGGC AAACAGAGTC CTTTGAGACA       1200

ACTTCAGGTT TAAGGTGTGG TGCTTTTACA CCTCGTGGTA ATTCGAACTA TTACCCTGGT       1260

TATTTTATCC GTAATATTTC TGGTGTTTCT TTAGTTCTTA GAAATGAAGA CTTAAAAAGA       1320

CCGTTATACT ATAACGAAAA AAGGAATATA GAAAGCCCTT CAGGAACACC TGGTGGAGCA       1380

AGAGCTTATA TGGTATCTGT GCATAACAAA AAAAATAACA TTTATGCAGT TCATGAAAAT       1440

GGTACTATGA TTCATTTAGC GCCGGAAGAT AATACAGGAT TTACTATATC ACCGATACAT       1500

GCCACTCAAG TGAATAATCA AACGCGAACA TTTATTTCCG AAAAATTTGG AAATCAAAGT       1560

GATTCCTTAA GATTTGAACA AAGCAACACG ACAGCTCGTT ATACCCTTAG AGGGAATGGA       1620

AATAGTTACA ATCTTTATTT AAGAGTATCT TCAATAGGAA ATTCCACTAT TCGAGTTACT       1680

ATAAACGGTA GAGTTTATAC TGCTTCAAAT GTTAATACTA CTACAAATAA CGATGGAGTT       1740

AATGATAACG GAGCTCGTTT TTCAGATATT AATATCGGTA ATGTAGTAGC AAGTAGTAAT       1800

TCTGATGTAC CATTAGATAT AAATGTAACA TTAAACTCCG GTACTCAATT TGATCTTATG       1860

AATATTATGC TTGTACCAAC TAATCTTCCA CCACTTTATT AA                          1902
```

(2) INFORMATION FOR SEQ ID NO:8:

(i) SEQUENCE CHARACTERISTICS:
        (A) LENGTH: 633 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Met Asn Asn Val Leu Asn Ser Gly Arg Asn Thr Ile Cys Asp Ala Tyr
 1               5                  10                  15

Asn Val Val His Asp Pro Phe Ser Phe Gln His Lys Ser Leu Asp
             20                  25                  30

Thr Ile Gln Lys Glu Trp Met Glu Trp Lys Lys Asp Asn His Ser Leu
         35                  40                  45

Tyr Val Asp Pro Ile Val Gly Thr Val Ala Ser Phe Leu Leu Lys Lys
     50                  55                  60

Leu Gly Ser Leu Ile Gly Lys Arg Ile Leu Ser Glu Leu Arg Asn Leu
 65                  70                  75                  80

Ile Phe Pro Ser Gly Ser Thr Asn Leu Met Glu Asp Ile Leu Arg Glu
                 85                  90                  95

Thr Glu Lys Phe Leu Asn Gln Lys Leu Asn Thr Asp Thr Leu Ser Arg
            100                 105                 110

Val Asn Ala Glu Leu Thr Gly Leu Gln Ala Asn Val Glu Glu Phe Asn
        115                 120                 125

Arg Gln Val Asp Asn Phe Leu Asn Pro Asn Arg Asn Ala Val Pro Leu
    130                 135                 140
```

-continued

```
Ser Ile Thr Ser Ser Val Asn Thr Met Gln Gln Leu Phe Leu Asn Arg
145                 150                 155                 160

Leu Ser Gln Phe Gln Met Gln Gly Tyr Gln Leu Leu Leu Leu Pro Leu
                165                 170                 175

Phe Ala Gln Ala Ala Asn Leu His Leu Ser Phe Ile Arg Asp Val Ile
            180                 185                 190

Leu Asn Ala Glu Glu Trp Gly Ile Ser Ala Ala Thr Leu Arg Thr Tyr
        195                 200                 205

Gln Asn His Leu Arg Asn Tyr Thr Arg Asp Tyr Ser Asn Tyr Cys Ile
    210                 215                 220

Asp Thr Tyr Gln Thr Ala Phe Arg Gly Leu Asn Thr Arg Leu His Asp
225                 230                 235                 240

Met Leu Glu Phe Arg Thr Tyr Met Phe Leu Asn Val Phe Glu Tyr Val
                245                 250                 255

Ser Ile Trp Ser Leu Phe Lys Tyr Gln Ser Leu Leu Val Ser Ser Gly
                260                 265                 270

Ala Asn Leu Tyr Ala Ser Gly Ser Gly Pro Gln Gln Thr Gln Leu Phe
            275                 280                 285

Thr Ser Gln Asp Trp Pro Phe Leu Tyr Ser Leu Phe Gln Val Asn Ser
290                 295                 300

Asn Tyr Val Leu Ser Gly Phe Ser Gly Ala Ser Leu Phe Thr Thr Phe
305                 310                 315                 320

Pro Asn Ile Gly Gly Leu Pro Gly Ser Thr Thr Thr Gln Ala Leu Leu
                325                 330                 335

Ala Ala Arg Val Asn Tyr Ser Gly Gly Ile Thr Ser Gly Ser Ile Gly
            340                 345                 350

Gly Ser Asn Phe Asn Gln Asn Phe Asn Cys Asn Thr Ile Ser Pro Pro
        355                 360                 365

Leu Ser Thr Ser Phe Val Arg Ile Trp Leu Asp Ser Gly Ser Asp Arg
    370                 375                 380

Gln Gly Val Thr Thr Val Thr Asn Trp Gln Thr Glu Ser Phe Glu Thr
385                 390                 395                 400

Thr Ser Gly Leu Arg Cys Gly Ala Phe Thr Pro Arg Gly Asn Ser Asn
                405                 410                 415

Tyr Tyr Pro Gly Tyr Phe Ile Arg Asn Ile Ser Gly Val Ser Leu Val
                420                 425                 430

Leu Arg Asn Glu Asp Leu Lys Arg Pro Leu Tyr Tyr Asn Glu Lys Arg
        435                 440                 445

Asn Ile Glu Ser Pro Ser Gly Thr Pro Gly Gly Ala Arg Ala Tyr Met
    450                 455                 460

Val Ser Val His Asn Lys Lys Asn Asn Ile Tyr Ala Val His Glu Asn
465                 470                 475                 480

Gly Thr Met Ile His Leu Ala Pro Glu Asp Asn Thr Gly Phe Thr Ile
                485                 490                 495

Ser Pro Ile His Ala Thr Gln Val Asn Asn Gln Thr Arg Thr Phe Ile
                500                 505                 510

Ser Glu Lys Phe Gly Asn Gln Ser Asp Ser Leu Arg Phe Glu Gln Ser
        515                 520                 525

Asn Thr Thr Ala Arg Tyr Thr Leu Arg Gly Asn Gly Asn Ser Tyr Asn
    530                 535                 540

Leu Tyr Leu Arg Val Ser Ser Ile Gly Asn Ser Thr Ile Arg Val Thr
545                 550                 555                 560
```

```
       Ile Asn Gly Arg Val Tyr Thr Ala Ser Asn Val Asn Thr Thr Thr Asn
                       565                 570                 575

Asn Asp Gly Val Asn Asp Asn Gly Ala Arg Phe Ser Asp Ile Asn Ile
                   580                 585                 590

Gly Asn Val Val Ala Ser Ser Asn Ser Asp Val Pro Leu Asp Ile Asn
                   595                 600                 605

Val Thr Leu Asn Ser Gly Thr Gln Phe Asp Leu Met Asn Ile Met Leu
               610                 615                 620

Val Pro Thr Asn Leu Pro Pro Leu Tyr
       625                 630

(2) INFORMATION FOR SEQ ID NO:9:

(i) SEQUENCE CHARACTERISTICS:
          (A) LENGTH: 1902 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:9:

ATGAATAATG TATTGAATAA TGGAAGAAAT ACTATTTGTG ATGCGTATAA TGTAGTGGTT      60

CATGATCCAT TTAGTTTTCA ACATAAATCA TTAGATACCA TACAAAAAGA ATGGATGGAG     120

TGGAAAAAAG ATAATCATAG TTTATATGTA GATCCTATTG TTGGAACTGT GGCTAGTTTT     180

CTGTTAAAGA AATTGGGGAG CCTTATTGGA AAACGGATAC TGAGTGAATT ACGGAATTTA     240

ATATTTCCTA GTGGCAGTAC AAATCTAATG GAAGATATTT TAAGAGAGAC AGAAAAATTC     300

CTAAATCAAA AACTTAATAC AGACACTCTT TCCCGTGTAA ATGCGGAATT GACAGGGCTG     360

CAAGCAAATG TAGAAGAGTT TAATCGACAA GTAGATAATT TTTTGAACCC TAACCGAAAC     420

GCTGTTCCTT TATCAATAAC TTCTTCAGTT AATACAATGC AGCAATTATT TCTAAATAGA     480

TTATCCCAGT TCCAGATGCA AGGATACCAA CTGTTATTAT TACCTTTATT TGCACAGGCA     540

GCCAATATAC ATCTTTCTTA TATTAGAGAT GTTATTCTTA ATGCAGAAGA ATGGGGCATT     600

TCAGCAGCAA CATTACGTAC GTATCAAAAT CACCTGAGAA ATTATACAAG AGATTACTCT     660

AATTATTGTA TAGATACGTA TCAAACTGCG TTTAGAGGTT TAAACACCCG TATACACGAT     720

ATGTTAGAAT TTAGAACATA TATGTTTTTA AATGTATTTG AATATGTATC TATCTGGTCG     780

TTGTTTAAAT ATCAAAGTCT TCTAGTATCT TCTGGCGCTA ATTTATATGC AAGTGGTAGT     840

GGACCACAGC AGACCCAATT ATTTACTTCA CAAGACTGGC CATTTTTATA TTCTCTTTTC     900

CAAGTTAATT CGAATTATGT ATTATCCGGC TTTAGTGGGG CTAGTCTTTT TACTACCTTT     960

CCTAATATTG GTGGCTTACC TGGTTCTACT ACAACTCAAG CATTACTTGC TGCAAGGGTT    1020

AATTATAGTG GAGGAATTAC ATCTGGTAGT ATAGGGGGTT CTAATTTTAA TCAAAATTTT    1080

AATTGCAACA CGATATCGCC ACCTTTGTCA ACGTCATTTG TTAGAAGTTG GCTAGATTCG    1140

GGTTCAGATC GACAGGGCGT TACTACCGTT ACAAATTGGC AAACAGAGTC CTTTGAGACA    1200

ACTTCAGGTT TAAGGTGTGG TGCTTTTACA CCTCGTGGTA ATTCGAACTA TTACCCTGGT    1260

TATTTTATCC GTAATATTTC TGGTGTTTCT TTAGTTCTTA GAAATGAAGA CTTAAAAAGA    1320

CCGTTATACT ATAACGAAAA AAGGAATATA GAAAGCCCTT CAGGAACACC TGGTGGAGCA    1380

AGAGCTTATA TGGTATCTGT GCATAACAAA AAAAATAACA TTTATGCAGT TCATGAAAAT    1440

GGTACTATGA TTCATTTAGC GCCGGAAGAT AATACAGGAT TTACTATATC ACCGATACAT    1500

GCCACTCAAG TGAATAATCA AACGCGAACA TTTATTTCCG AAAAATTTGG AAATCAAGGT    1560
```

```
GATTCCTTAA GATTTGAACA AAGCAACACG ACAGCTCGTT ATACCCTTAG AGGGAATGGA    1620

AATAGTTACA ATCTTTATTT AAGAGTATCT TCAATAGGAA ATTCCACTAT TCGAGTTACT    1680

ATAAACGGTA GAGTTTATAC TGCTTCAAAT GTTAATACTA CTACAAATAA CGATGGAGTT    1740

AATGATAACG GAGCTCGTTT TTCAGATATT AATATCGGTA ATGTAGTAGC AAGTAGTAAT    1800

TCTGATGTAC CATTAGATAT AAATGTAACA TTAAACTCCG GTACTCAATT TGATCTTATG    1860

AATATTATGC TTGTACCAAC TAATATTTCA CCACTTTATT AA                      1902
```

(2) INFORMATION FOR SEQ ID NO:10:

(i) SEQUENCE CHARACTERISTICS:
        (A) LENGTH: 633 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Met Asn Asn Val Leu Asn Asn Gly Arg Asn Thr Ile Cys Asp Ala Tyr
  1               5                  10                  15

Asn Val Val His Asp Pro Phe Ser Phe Gln His Lys Ser Leu Asp
             20                  25                  30

Thr Ile Gln Lys Glu Trp Met Glu Trp Lys Lys Asp Asn His Ser Leu
             35                  40                  45

Tyr Val Asp Pro Ile Val Gly Thr Val Ala Ser Phe Leu Leu Lys Lys
         50                  55                  60

Leu Gly Ser Leu Ile Gly Lys Arg Ile Leu Ser Glu Leu Arg Asn Leu
 65                  70                  75                  80

Ile Phe Pro Ser Gly Ser Thr Asn Leu Met Glu Asp Ile Leu Arg Glu
                 85                  90                  95

Thr Glu Lys Phe Leu Asn Gln Lys Leu Asn Thr Asp Thr Leu Ser Arg
                100                 105                 110

Val Asn Ala Glu Leu Thr Gly Leu Gln Ala Asn Val Glu Glu Phe Asn
            115                 120                 125

Arg Gln Val Asp Asn Phe Leu Asn Pro Asn Arg Asn Ala Val Pro Leu
        130                 135                 140

Ser Ile Thr Ser Ser Val Asn Thr Met Gln Gln Leu Phe Leu Asn Arg
145                 150                 155                 160

Leu Ser Gln Phe Gln Met Gln Gly Tyr Gln Leu Leu Leu Leu Pro Leu
                165                 170                 175

Phe Ala Gln Ala Ala Asn Ile His Leu Ser Tyr Ile Arg Asp Val Ile
            180                 185                 190

Leu Asn Ala Glu Glu Trp Gly Ile Ser Ala Ala Thr Leu Arg Thr Tyr
        195                 200                 205

Gln Asn His Leu Arg Asn Tyr Thr Arg Asp Tyr Ser Asn Tyr Cys Ile
    210                 215                 220

Asp Thr Tyr Gln Thr Ala Phe Arg Gly Leu Asn Thr Arg Ile His Asp
225                 230                 235                 240

Met Leu Glu Phe Arg Thr Tyr Met Phe Leu Asn Val Phe Glu Tyr Val
                245                 250                 255

Ser Ile Trp Ser Leu Phe Lys Tyr Gln Ser Leu Leu Val Ser Ser Gly
            260                 265                 270

Ala Asn Leu Tyr Ala Ser Gly Ser Gly Pro Gln Gln Thr Gln Leu Phe
        275                 280                 285
```

```
Thr Ser Gln Asp Trp Pro Phe Leu Tyr Ser Leu Phe Gln Val Asn Ser
    290                 295                 300

Asn Tyr Val Leu Ser Gly Phe Ser Gly Ala Ser Leu Phe Thr Thr Phe
305                 310                 315                 320

Pro Asn Ile Gly Gly Leu Pro Gly Ser Thr Thr Thr Gln Ala Leu Leu
                325                 330                 335

Ala Ala Arg Val Asn Tyr Ser Gly Gly Ile Thr Ser Gly Ser Ile Gly
            340                 345                 350

Gly Ser Asn Phe Asn Gln Asn Phe Asn Cys Asn Thr Ile Ser Pro Pro
        355                 360                 365

Leu Ser Thr Ser Phe Val Arg Ser Trp Leu Asp Ser Gly Ser Asp Arg
    370                 375                 380

Gln Gly Val Thr Thr Val Thr Asn Trp Gln Thr Glu Ser Phe Glu Thr
385                 390                 395                 400

Thr Ser Gly Leu Arg Cys Gly Ala Phe Thr Pro Arg Gly Asn Ser Asn
                405                 410                 415

Tyr Tyr Pro Gly Tyr Phe Ile Arg Asn Ile Ser Gly Val Ser Leu Val
            420                 425                 430

Leu Arg Asn Glu Asp Leu Lys Arg Pro Leu Tyr Tyr Asn Glu Lys Arg
        435                 440                 445

Asn Ile Glu Ser Pro Ser Gly Thr Pro Gly Gly Ala Arg Ala Tyr Met
    450                 455                 460

Val Ser Val His Asn Lys Lys Asn Ile Tyr Ala Val His Glu Asn
465                 470                 475                 480

Gly Thr Met Ile His Leu Ala Pro Glu Asp Asn Thr Gly Phe Thr Ile
                485                 490                 495

Ser Pro Ile His Ala Thr Gln Val Asn Asn Gln Thr Arg Thr Phe Ile
                500                 505                 510

Ser Glu Lys Phe Gly Asn Gln Gly Asp Ser Leu Arg Phe Glu Gln Ser
        515                 520                 525

Asn Thr Thr Ala Arg Tyr Thr Leu Arg Gly Asn Gly Asn Ser Tyr Asn
    530                 535                 540

Leu Tyr Leu Arg Val Ser Ser Ile Gly Asn Ser Thr Ile Arg Val Thr
545                 550                 555                 560

Ile Asn Gly Arg Val Tyr Thr Ala Ser Asn Val Asn Thr Thr Thr Asn
                565                 570                 575

Asn Asp Gly Val Asn Asp Asn Gly Ala Arg Phe Ser Asp Ile Asn Ile
            580                 585                 590

Gly Asn Val Val Ala Ser Ser Asn Ser Asp Val Pro Leu Asp Ile Asn
        595                 600                 605

Val Thr Leu Asn Ser Gly Thr Gln Phe Asp Leu Met Asn Ile Met Leu
    610                 615                 620

Val Pro Thr Asn Ile Ser Pro Leu Tyr
625                 630
```